United States Patent
Zhao et al.

(10) Patent No.: US 10,618,939 B2
(45) Date of Patent: Apr. 14, 2020

(54) HYDROCARBON-STAPLED POLYPEPTIDES FOR ENHANCEMENT OF ENDOSOME-LYSOSOMAL DEGRADATION

(71) Applicant: The Hong Kong Polytechnic University, Hong Kong (CN)

(72) Inventors: Yanxiang Zhao, Hong Kong (CN); Shuai Wu, Hong Kong (CN); Wenchao Yang, Hong Kong (CN); Yunjiao He, Hong Kong (CN); Xiaohua Li, Hong Kong (CN); Xianxiu Qiu, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 9 days.

(21) Appl. No.: 15/921,576

(22) Filed: Mar. 14, 2018

(65) Prior Publication Data

US 2018/0208627 A1      Jul. 26, 2018

Related U.S. Application Data

(63) Continuation-in-part of application No. 15/636,999, filed on Jun. 29, 2017, now abandoned.

(60) Provisional application No. 62/355,883, filed on Jun. 29, 2016.

(51) Int. Cl.
C07K 7/08        (2006.01)
A61P 35/00       (2006.01)

(52) U.S. Cl.
CPC .............. C07K 7/08 (2013.01); A61P 35/00 (2018.01)

(58) Field of Classification Search
CPC ...... C07K 7/08; C07K 14/4747; A61K 38/00; A61P 35/00
See application file for complete search history.

(56) References Cited

U.S. PATENT DOCUMENTS 8,802,633 B1     8/2014 Levine et al.
2005/0250680 A1* 11/2005 Walensky ............ C07K 14/001
                                                 514/18.9

FOREIGN PATENT DOCUMENTS

WO    WO-2012037547 A2 *  3/2012   ........... A61K 31/365

OTHER PUBLICATIONS

Li et al., Imperfect interface of Beclin1 coiled-coil domain regulates homodimer and heterodimer formation with Atg14L and UVRAG, Nature Communications, vol. 3:662 doi:10.1038/ncomms1648 (11 pages) (Feb. 7, 2012) (Year: 2012).*

Walensky et al., Hydrocarbon-Stapled Peptides: Principles, Practice, and Progress, Journal of Medicinal Chemistry, vol. 57:6275-6288 (2014) (Year: 2014).*

(Continued)

Primary Examiner — Randall L Beane
(74) Attorney, Agent, or Firm — Law Offices of Albert Wai-Kit Chan, PLLC

(57) ABSTRACT

The present invention relates to a Beclin 1-UVRAG complex structure which reveals a tightly packed coiled coil assembly with Beclin 1 and UVRAG residues complementing each other to form a stable dimeric complex. This potent physical interaction is critical for UVRAG-dependent EGFR degradation but less critical for autophagy. Targeting the Beclin 1 coiled coil domain with rationally designed stapled peptides leads to enhanced autophagy activity and EGFR degradation in non-small cell lung cancer (NSCLC) cell lines, suggesting translational value for these compounds.

9 Claims, 7 Drawing Sheets
Specification includes a Sequence Listing.

(56) References Cited

OTHER PUBLICATIONS

Wei et al., EGFR-mediated Beclin 1 phosphorylation in autophagy suppression, tumor progression, and tumor chemoresistance, Cell. vol. 154(6):1269-1284 (Sep. 2013) (Year: 2013).*
Cochran, Antagonists of protein-protein interactions, Chemistry & Biology, vol. 7:R85-R94 (2000); (Year: 2000).*
Zhang et al., Antiviral activity of α-helical stapled peptides designed from the HIV-1 capsid dimerization domain, Retrovirology, vol. 8(28):1-18 (2011) (Year: 2011).*
Araghi et al., Designing helical peptide inhibitors of protein-protein interactions, Current Opinion in Structural Biology, vol. 39:27-38 (Apr. 25, 2016) (Year: 2016).*
Adi-Harel et al.; Beclin 1 self-association is independent of autophagy induction by amino acid deprivation and rapamycin treatment; J Cell Biochem. Aug. 1, 2010;110(5):1262-71. doi: 10.1002/jcb.22642.
Bricogne et al.; Generation, representation and flow of phase information in structure determination: recent developments in and around SHARP 2.0; Acta Crystallogr D Biol Crystallogr. Nov. 2003;59(Pt 11):2023-30. Epub Oct. 23, 2003.
Emsley et al.; Coot: model-building tools for molecular graphics; Acta Crystallogr D Biol Crystallogr. Dec. 2004;60(Pt 12 Pt 1):2126-32. Epub Nov. 26, 2004.
High-throughput structure determination. Proceedings of the 2002 CCP4 (Collaborative Computational Project in Macromolecular Crystallography) study weekend. Jan. 2002. York, United Kingdom. Acta Crystallogr D Biol Crystallogr. Nov. 2002;58(Pt 11):1897-970.
He et al.; The Beclin 1 interactome; Curr Opin Cell Biol. Apr. 2010;22(2):140-9. doi: 10.1016/j.ceb.2010.01.001, Epub Jan. 22, 2010.
Kim et al.; Synthesis of all-hydrocarbon stapled α-helical peptides by ring-closing olefin metathesis; Nat Protoc. Jun. 2011;6(6):761-71. doi: 10.1038/nprot.2011.324. Epub May 12, 2011.
Li et al.; The BECN1 coiled coil domain: an "imperfect" homodimer interface that facilitates ATG14 and UVRAG binding; Autophagy. Aug. 2012;8(8):1258-60. doi: 10.4161/auto.20750. Epub May 31, 2012.
Liang et al.; Beclin1-binding UVRAG targets the class C Vps complex to coordinate autophagosome maturation and endocytic trafficking; Nat Cell Biol. Jul. 2008;10(7):776-87. doi: 10.1038/ncb1740. Epub Jun. 15, 2008.
Liang et al.; Beyond autophagy: the role of UVRAG in membrane trafficking; Autophagy. Aug. 2008;4(6):817-20. Epub Jun. 25, 2008.
Liang et al.; UVRAG: a new player in autophagy and tumor cell growth; Autophagy. Jan.-Feb. 2007;3(1):69-71, Epub Jan. 27, 2007.
Liang et al.; Autophagic and tumour suppressor activity of a novel Beclin1-binding protein UVRAG; Nat Cell Biol. Jul. 2006;8(7):688-99. Epub Jun. 25, 2006.
Matsunaga et al.; Two Beclin 1-binding proteins, Atg14L and Rubicon, reciprocally regulate autophagy at different stages; Nat Cell Biol. Apr. 2009;11(4):385-96. doi: 10.1038/ncb1846. Epub Mar. 8, 2009.
McKnight et al.; Beclin 1 is required for neuron viability and regulates endosome pathways via the UVRAG-VPS34 complex; PLoS Genet. Oct. 2, 2014;10(10):e1004626. doi: 10.1371/journal.pgen.1004626. eCollection Oct. 2014.
Murshudov et al.; Refinement of macromolecular structures by the maximum-likelihood method; Acta Crystallogr D Biol Crystallogr. May 1, 1997;53(Pt 3):240-55.
Noble et al.; Bcl-xL and UVRAG cause a monomer-dimer switch in Beclin1; J Biol Chem. Sep. 19, 2008;283(38):26274-82. doi: 10.1074/jbc.M804723200. Epub Jul. 18, 2008.
Otwinowski et al.; Processing of X-ray diffraction data collected in oscillation mode; Methods Enzymol. 1997;276:307-326, doi: 10.1016/S0076-6879(97)76066-X.
Perelman et al.; Molecular cloning of a novel human gene encoding a 63-kDa protein and its sublocalization within the 11q13 locus; Genomics, May 1, 1997;41(3):397-405.
Potterton et al.; Developments in the CCP4 molecular-graphics project; Acta Crystallogr D Biol Crystallogr. Dec. 2004;60(Pt 12 Pt 1):2288-94. Epub Nov. 26, 2004.
Rostislavleva et al.; Structure and flexibility of the endosomal Vps34 complex reveals the basis of its function on membranes; Science. Oct. 9, 2015;350(6257):aac7365. doi: 10.1126/science.aac7365.
Takahashi et al.; Bif-1/endophilin B1: a candidate for crescent driving force in autophagy; Cell Death Differ. Jul. 2009;16(7):947-55, doi: 10.1038/cdd.2009.19. Epub Mar. 6, 2009.
Takahashi et al.; Bif-1 interacts with Beclin 1 through UVRAG and regulates autophagy and tumorigenesis; Nat Cell Biol. Oct. 2007;9(10);1142-51. Epub Sep. 23, 2007.
Terwilliger et al.; Automated MAD and MIR structure solution; Acta Crystallogr D Biol Crystallogr. Apr. 1999;55(Pt 4):849-61.
Zhao et al.; A dual role for UVRAG in maintaining chromosomal stability; Dev Cell. May 15, 2012;22(5):1001-16. doi: 10.1016/j.devcel.2011.12.027. Epub Apr. 26, 2012.
Zhong et al.; Distinct regulation of autophagic activity by Atg14L and Rubicon associated with Beclin 1-phosphatidylinositol-3-kinase complex; Nat Cell Biol. Apr. 2009;11(4):468-76. doi: 10.1038/ncb1854. Epub Mar. 8, 2009.

* cited by examiner

Figure 1C

| Number | Sequence | Interaction energy (kcal/mol) |
|--------|----------|-------------------------------|
| SP1 | Ac-RLIQEL(R8)DREAQR(S5)V-NH₂ | -29.75±6.62 |
| SP2 | Ac-RLIQEL(R8)DREAQR(S5)S-NH₂ | -43.69±5.21 |
| SP3 | Ac-RLISEL(R8)DREKQR(S5)V-NH₂ | -47.51±3.96 |
| SP4 | Ac-RLISEL(R8)DREKQR(S5)A-NH₂ | -56.05±6.87 |
| SP5 | Ac-RLIQEL(R8)DREKQR(S5)S-NH₂ | -40.75±5.59 |
| SP6 | Ac-RLISEL(R8)DREKQR(S5)S-NH₂ | -47.40±6.90 |
| SP7 | Ac-RLIQEL(R8)DREKQR(S5)R-NH₂ | -45.77±5.13 |
| SP8 | Ac-RLIQEL(R8)DREKER(S5)A-NH₂ | -49.78±6.34 |
| SP9 | Ac-LLSEL(R8)DREKQR(S5)A-NH₂ | -74.52±4.31 |
| SP10 | Ac-RLLSEL(R8)DREKQR(S5)A-NH₂ | -55.69±5.15 |
| SP11 | Ac-LLLSRL(R8)DREKQR(S5)A-NH₂ | -50.47±5.23 |
| SP12 | Ac-LLISQL(R8)DREKQR(S5)A-NH₂ | -56.05±4.35 |

HYDROCARBON-STAPLED POLYPEPTIDES FOR ENHANCEMENT OF ENDOSOME-LYSOSOMAL DEGRADATION

CROSS-REFERENCE TO RELATED APPLICATIONS

This application is a continuation-in-part application of U.S. patent applicant Ser. No. 15/636,999, filed Jun. 29, 2017, which claims the benefit of U.S. Provisional Application No. 62/355,883, filed Jun. 29, 2016. The entire contents and disclosures of the preceding applications are hereby incorporated by reference into this application.

Throughout this application, various publications are cited. The disclosures of these publications in their entireties are hereby incorporated by reference into this application to more fully describe the state of the art to which this invention pertains.

FIELD OF THE INVENTION

This invention relates to designed peptide analogs that promote autophagy by specifically targeting the Beclin 1-Vps34 complex.

BACKGROUND OF THE INVENTION

UV irradiation resistance-associated gene (UVRAG) has been implicated in diverse cellular processes including autophagy, endocytic trafficking and chromosome maintenance. UVRAG was first identified from a cDNA library screening for its ability to complement partially the ultraviolet sensitivity of a xeroderma pigmentosum cell line (Perelman et al., 1997). UVRAG was recently found to be a key regulator of the Class III Phosphotidylinositol 3-Kinase (PI3K) complex, a critical component of the molecular machinery of autophagy consisting of the scaffolding protein Beclin 1 and the lipid kinase VPS34 as core members. Through potent and specific interaction with Beclin 1, UVRAG can lead to the formation of UVRAG-containing Beclin 1-VPS34 complex with enhanced lipid kinase activity to direct VPS34-related cellular processes such as autophagy (Liang et al., 2006; Liang et al., 2007). UVRAG has also been found to associate with Class C Vps complex and coordinate endocytic trafficking (Liang et al., 2008a; Liang et al., 2008b). Furthermore, UVRAG plays a role in maintaining structural integrity and proper segregation of chromosomes through its interactions with centrosome protein CEP63 and DNA-PK that is involved in homologous end joining (Zhao et al., 2012).

UVRAG contains two well predicted functional domains based on sequence alignment. The N-terminal C2 domain is regarded to associate with membrane and be involved in autophagy and endosomal trafficking (Liang et al., 2006). The coiled coil (CC) domain is critical for binding to Beclin 1, the essential autophagy scaffolding protein, to form the autophagy-promoting UVRAG-containing Beclin 1-VPS34 complex (Liang et al., 2006). In addition to these two domains, the N-terminal proline-rich sequence of UVRAG interacts with the SH3 domain of Bif-1 and probably enables Bif-1 to promote autophagosome formation through its membrane-curving BAR domain (Takahashi et al., 2007; Takahashi et al., 2009). The region between the coiled coil domain and the C-terminal PEST-like sequence is involved in interaction with Class C Vps complex, CEP63 and DNA-PK (Liang et al., 2008a; Zhao et al., 2012).

No structural information at atomic resolution is currently available regarding UVRAG, and the molecular mechanism of how the individual functional domains of UVRAG associate with their respective binding partners to regulate diverse cellular processes of autophagy, endocytic trafficking and chromosomal segregation is not well understood.

The interaction between Beclin 1 and two central autophagy regulators Atg14L and UVRAG is mediated through their respective coiled coil domains (Liang et al., 2006; Matsunaga et al., 2009; Zhong et al., 2009). The structure of the Beclin 1 coiled coil domain was determined previously, which forms a metastable antiparallel coiled coil structure due to several charged or polar residues that destabilize an otherwise hydrophobic dimer interface (Li et al., 2012a). This metastability is found to be important for Beclin 1's interaction with Atg14L or UVRAG because it enables the homodimeric Beclin 1 to readily dissociate and form heterodimeric assembly with Atg14L and UVRAG (Li et al., 2012a). Mutations within the Beclin 1 coiled coil domain that render it monomeric retains its binding to Atg14L or UVRAG and facilitates normal autophagy induction; while mutations that stabilize the Beclin 1 homodimer weaken or abolish its interaction with Atg14L and lead to impaired autophagosome formation (Li et al., 2012a; Li et al., 2012b).

The mammalian Class III phosphatidylinositol 3-kinase (PI3KC3) complex, also termed the Beclin 1-Vps34 complex, is a dynamic multi-protein assembly that plays critical roles in membrane-mediated intracellular transportation processes such as autophagy, endocytic trafficking and phagocytosis. Core members of this complex include the lipid kinase Vps34 that serves as the major producer of phosphatidylinositol 3-phosphate (PI3P) lipids; a serine/threonine kinase Vps15 stably associated with Vps34, the scaffolding molecule Beclin 1 and either Atg14L or UVRAG as the Beclin 1-binding partner. The Atg14L-containing form is termed Beclin 1-Atg14L complex and mainly involved in early-stage autophagy induction because Atg14L is responsible for directing Beclin 1-Atg14L complex to ER sites to promote autophagosome biogenesis. The UVRAG-containing form, on the other hand, is termed Beclin 1-UVRAG complex and plays critical roles in late-stage autophagy execution and degradative endocytic trafficking. In addition to these core molecules, many regulators such as Ambra1, Bcl-2, NRBF2 and Rubicon can associate with the Beclin 1-Vps34 complex in dynamic and context-dependent manner to exert modulatory effect on the Vps34 kinase activity. The molecular mechanism of such regulation, particularly whether these diverse molecules share a common theme of modulating the structural and thus biochemical properties of the Beclin 1-Vps34 complex, is not well understood.

SUMMARY OF THE INVENTION

The present invention discloses a hydrocarbon-stapled polypeptide designed to target a polypeptide comprising amino acid residues 231-245 of rat Beclin 1 (SEQ ID NO: 15: YSEFKRQQLELDDEL), or amino acids 233-247 of human Beclin 1 (SEQ ID NO: 16: YSEFKRQQLELDDEL), wherein the hydrocarbon-stapled polypeptide comprises an amino acid sequence that is at least 85% identical to amino acid residues 191-205 of rat Beclin 1 (SEQ ID NO: 17: RLIQELEDVEKNRKV), or amino acids 193-207 of human Beclin 1 (SEQ ID NO: 18: RLIQELEDVEKNRKI).

The present invention discloses a pharmaceutical composition comprising the hydrocarbon-stapled polypeptide of the present invention.

The present invention also discloses a method of enhancing autophagy or endocytic trafficking, comprising the step of contacting a population of cells with the hydrocarbon-stapled polypeptide of the present invention, thereby enhancing lysosomal degradation of one or more target proteins.

The present invention further discloses a method of inhibiting cancer cell growth, comprising administering the hydrocarbon-stapled polypeptide of the present invention to a subject in need thereof.

BRIEF DESCRIPTION OF THE DRAWINGS

FIG. 1C shows computational modeling to optimize the amino acid sequence of designed stapled peptides. The residues deemed critical for Beclin 1 binding are marked with "*" and remain unchanged. Residues subject to computational mutation are marked with "A". Molecular dynamics (MD) simulations were conducted to evaluate the binding modes of the designed peptides, and the binding energies were computed using the force field-based MM-GB/SA method. Three highlighted candidates, SP4 (SEQ ID NO: 4), SP9 (SEQ ID NO: 9) and SP12 (SEQ ID NO: 12) show significantly improved binding as compared to SP1 (SEQ ID NO: 1).

DETAILED DESCRIPTION OF THE INVENTION

Figure 1A:
FIG. 1A shows the design principle of Beclin 1-specific α-helical stapled peptides. The coiled coil domains of Beclin 1 and UVRAG are drawn in relative scale to demonstrate the hydrophobic interface formed between the N-terminal half of Beclin 1 coiled coil domain and UVRAG. The stapled peptide is shown as a short ribbon. The spheres on the ribbon represent the chemically engineered staples to stabilize the α-helical structure. The two Ys mark Beclin 1 residue Y227 and Y231, which correspond to the EGFR-phosphorylated Y229 and Y233 in human Beclin 1. The stapled peptide is designed to bind to the C-terminal half of Beclin 1 coiled coil region starting from around Y227 and Y231.

The present invention discloses formation of a more stable heterodimeric coiled coil assembly of Beclin 1 and UVRAG. The present invention further relates to enhanced VPS lipid kinase activity and autophagy induction by the stable Beclin 1-UVRAG complex.

Furthermore, structure-based rational design of Beclin 1-targeting stapled peptides are investigated. The present invention further discloses rationally designed stapled peptides that can promote autophagy and enhance EGFR degradation.

In one embodiment, the sequence of the peptide can be computationally optimized to achieve specific Beclin 1 interaction. In one embodiment, hydrocarbon staples are designed to stabilize the peptide structure. In another embodiment, future modification or improvements of the stapled peptide can be done by improving the potency of the designed peptides by, for example, varying the amino acid composition or adding functional groups.

In one embodiment, Beclin 1-specific stapled peptides that promotes autophagy and enhances lysosomal degradation of EGFR were designed.

In some embodiments, the peptides of the present invention can be used for anti-EGFR therapy. In a further embodiment, the peptides designed by the present invention can be used to target EGFR degradation by enhancing the Beclin 1-UVRAG interaction. In one embodiment, the peptides designed by the present invention help to enhance EGFR degradation so as to reduce EGFR signaling and inhibit cell proliferation. In one embodiment, the peptides designed by the present invention can be used in anti-cancer therapy for EGFR-driven tumor types like non-small cell lung cancer (NSCLC), colorectal cancer, ovarian cancer, glioblastoma and breast cancer. In another embodiment, the present invention serves as orthogonal approach to existing NSCLC treatment regiments. In one embodiment, the peptides of the present invention can be used for treatment of neurodegenerative diseases where autophagy enhancement would be beneficial.

The present invention discloses a hydrocarbon-stapled polypeptide designed to target a polypeptide comprising amino acid residues 231-245 of rat Beclin 1 (SEQ ID NO: 15), or amino acids 233-247 of human Beclin 1 (SEQ ID NO: 16), wherein the hydrocarbon-stapled polypeptide comprises an amino acid sequence that is at least 85% identical to amino acid residues 191-205 of rat Beclin 1 (SEQ ID NO: 17), or amino acids 193-207 of human Beclin 1 (SEQ ID NO: 18). In one embodiment, the hydrocarbon-stapled polypeptide comprises an amino acid sequence that is at least 90% identical to amino acid residues 191-205 of rat Beclin 1 (SEQ ID NO: 17), or amino acids 193-207 of human Beclin 1 (SEQ ID NO: 18). the hydrocarbon-stapled polypeptide comprises an amino acid sequence that is at least 95% identical to amino acid residues 191-205 of rat Beclin 1 (SEQ ID NO: 17), or amino acids 193-207 of human Beclin 1 (SEQ ID NO: 18).

In one embodiment, the hydrocarbon-stapled polypeptide is about 10-40 amino acids in length. In one embodiment, the hydrocarbon-stapled polypeptide is 10-30 amino acids in length. In one embodiment, the hydrocarbon-stapled polypeptide is 10-20 amino acids in length.

In one embodiment, the hydrocarbon-stapled polypeptide comprises one or more α,α-disubstituted 5-carbon olefinic amino acids. In one embodiment, the hydrocarbon-stapled polypeptide comprises one or more α,α-disubstituted 8-carbon olefinic amino acids. In one embodiment, the hydrocarbon-stapled polypeptide comprises unnatural amino acids at position i and position i+7. In one embodiment, the hydrocarbon-stapled polypeptide comprises a stabilized alpha-helix.

In one embodiment, the hydrocarbon-stapled polypeptide has an affinity for the polypeptide comprising amino acid residues 231-245 of rat Beclin 1 (SEQ ID NO: 15), or amino acids 233-247 of human Beclin 1 (SEQ ID NO: 16), of at least 5 µM. In one embodiment, the hydrocarbon-stapled polypeptide has an affinity for the polypeptide comprising amino acid residues 231-245 of rat Beclin 1 (SEQ ID NO: 15), or amino acids 233-247 of human Beclin 1 (SEQ ID NO: 16), of at least 2 µM.

In one embodiment, the hydrocarbon-stapled polypeptide has the sequence of one of SEQ ID NO. 1-12.

The present invention discloses a pharmaceutical composition comprising the hydrocarbon-stapled polypeptide of the present invention. The pharmaceutical composition of the present invention further comprises one or more pharmaceutically acceptable excipients, vehicles or carriers. In one embodiment, the pharmaceutical composition is formulated in the form of a cream, gel, ointment, suppository, tablet, granule, injection, powder, solution, suspension, spray, patch or capsule. In one embodiment, the pharmaceutical composition is administered orally, nasally, aurally, ocularly, sublingually, buccally, systemically, transdermally, mucosally, via cerebral spinal fluid injection, vein injection, muscle injection, peritoneal injection, subcutaneous injection, or by inhalation.

The present invention also discloses a method of enhancing autophagy or endocytic trafficking, comprising the step of contacting a population of cells with the hydrocarbon-stapled polypeptide of the present invention, thereby enhancing lysosomal degradation of one or more target proteins. In one embodiment, the target protein is EGFR. In one embodiment, the cells treated with the hydrocarbon-stapled polypeptide have decreased EGFR-driven cell proliferation.

The present invention further discloses a method of inhibiting cancer cell growth, comprising administering the hydrocarbon-stapled polypeptide of the present invention to a subject in need thereof. In one embodiment, the subject is a vertebrate, a mammal or human. In one embodiment, the cancer cell growth comprises EGFR-driven cell proliferation. In one embodiment, the cancer cells are non-small cell lung cancer cells, breast cancer cells, colon cancer cells, ovarian cancer cells, carcinoma cells, sarcoma cells, lung cancer cells, fibrosarcoma cells, myosarcoma cells, liposarcoma cells, chondrosarcoma cells, osteogenic sarcoma cells, chordoma cells, angiosarcoma cells, endotheliosarcoma cells, lymphangiosarcoma cells, lymphangioendotheliosarcoma cells, synovioma cells, mesothelioma cells, Ewing's tumor cells, leiomyosarcoma cells, rhabdomyosarcoma cells, gastric cancer cells, esophageal cancer cells, rectal cancer cells, pancreatic cancer cells, prostate cancer cells, uterine cancer cells, head and neck cancer cells, skin cancer cells, brain cancer cells, squamous cell carcinoma, sebaceous gland carcinoma cells, papillary carcinoma cells, papillary adenocarcinoma cells, cystadenocarcinoma cells, medullary carcinoma cells, bronchogenic carcinoma cells, renal cell carcinoma cells, hepatoma cells, bile duct carcinoma cells, choriocarcinoma cells, seminoma cells, embryonal carcinoma cells, Wilm's tumor cells, cervical cancer cells, testicular cancer cells, small cell lung carcinoma cells, bladder carcinoma cells, epithelial carcinoma cells, glioma cells, astrocytoma cells, medulloblastoma cells, craniopharyngioma cells, ependymoma cells, pinealoma cells, hemangioblastoma cells, acoustic neuroma cells, oligodendroglioma cells, meningioma cells, melanoma cells, neuroblastoma cells, retinoblastoma cells, T-cells or natural killer cells of leukemia, lymphoma cells, or Kaposi's sarcoma cells.

The invention will be better understood by reference to the Experimental Details which follow, but those skilled in the art will readily appreciate that the specific experiments are provided only for illustrative purpose and are not meant to limit the invention scope as described herein, which is defined by the claims following thereafter.

It is to be noted that the transitional term "comprising", which is synonymous with "including", "containing" or "characterized by", is inclusive or open-ended, and does not exclude additional, un-recited elements or method steps.

Example 1

Optimerization and Performance of Stapled Peptides

This example shows that the rationally optimized stapled peptide SP4 (SEQ ID NO: 4) can promote autophagy activity and enhance lysosomal degradation of EGFR in a Beclin 1-dependent manner in multiple cell lines.

1. Reagents

Chloroquine (CQ; Sigma-Aldrich), Epidermal Growth Factor (EGF; Invitrogen), anti-β-actin antibody (Santa Cruz Biotechnology), anti-Beclin 1 antibody (Santa Cruz Biotechnology), anti-Flag antibody (Sigma-Aldrich), anti-Flag M2 Magnetic Beads (Sigma-Aldrich), protein A/G PLUS agarose beads (Santa Cruz Biotechnology), anti-GFP antibody (Roche), anti-LC3 antibody (Abnova), anti-p62 antibody (Abnova), Anti-Mouse IgG-HRP (Sigma-Aldrich), Anti-Rabbit IgG-HRP (Sigma-Aldrich), Lipofectamine 2000 (Invitrogen), Protease inhibitor cocktail (Roche Diagnostics), trypsin (Invitrogen), isopropyl-β-D-thiogalactopyranoside (IPTG; Sigma-Aldrich), PVDF membrane (Millipore), Fluorescence mounting medium (Calbiochem).

2. Protein Expression and Purification

The various fragments of UVRAG coiled coil domain were amplified by PCR using *Mus musculus* pCMV-UVRAG-FL as template and subcloned into modified pET-32a vector containing the human rhinovirus 3C protease cleavage site and thioredoxin-6×His fusion. The linked Beclin 1-UVRAG coiled coil domain was constructed by inserting a "(Gly-Ser)5" segment between Beclin 1 coiled coil fragment (174-223) and UVRAG coiled coil fragment (228-275) (SEQ ID NO: 19) and subsequently cloned into the same vector. All protein constructs were expressed in

*Escherichia coli* BL21 (DE3) cells at 30° C. after induction by isopropyl-β-d-thiogalactopyranoside (IPTG) and purified by affinity chromatography (HisTrap HP, GE Healthcare). The fused tag was removed by 3C cleavage and the untagged protein was further purified by size-exclusion chromatography (Superdex 75, GE Healthcare).

3. Plasmid Constructs for Cell-Based Studies

Full length *Mus musculus* UVRAG wild type (SEQ ID NO: 20) was cloned into BamHI and XhoI sites of pcDNA3.1 Flag vector, HindIII and BamHI sites of pEGFP N3 vector and HindIII and BamHI sites of pmCherry N1 vector. Full length *Mus musculus* Atg14L was cloned into EcoRI and BamHI sites of pEGFP N3 vector following standard procedure.

4. Cell Culture

HEK293T, HeLa and A549 cell lines were cultured in Dulbecco's Modified Eagle's Medium (DMEM, Sigma) supplemented with 10% fetal bovine serum (FBS, Invitrogen). HeLa cell with stable expression of GFP-LC3 was a kind gift from Dr. Han Ming Shen's lab in National University of Singapore. All cell lines used in the experiments were *mycoplasma* detected negative by MycoAlert™ PLUS *Mycoplasma* Detection Kit (Lonza) before and during the experiment. Transient transfection was performed using Lipofectamine 2000 (Invitrogen) according to manufacturer's instruction.

5. Immunoblot Analysis

Transient DNA transfection was performed using Lipofectamine 2000 (Invitrogen). For Co-IP experiment to measure interaction between UVRAG and endogenous Beclin 1, FLAG-tagged UVRAG plasmids were transfected into HEK293T cells. For Co-IP experiments to demonstrate competition between UVRAG and Atg14L for binding to endogenous Beclin 1, equal amount of FLAG-tagged UVRAG mutant plasmids and GFP-tagged Atg14L plasmids or equal amounts of FLAG-tagged Atg14L plasmids and GFP-tagged UVRAG mutant plasmids were co-transfected into HEK293T cells. For immunoblotting assay of LC3-II, p62 and EGFR degradation, FLAG-tagged UVRAG mutant plasmids were transfected into HEK293T cells, HeLa cell stably expressing GFP-LC3 and A549 NSCLC cells respectively. Cells were lysed in IP buffer (25 mM HEPES PH 7.5, 10 mM MgCl2, 150 mM NaCl, 1 mM EDTA.2Na, 1% Nonidet P-40, 1% Triton X-100 and 2% glycerol) or Laemmli sample buffer (62.5 mM Tris-HCl, pH 6.8, 2% SDS, 25% glycerol, 5% β-mercaptoethanol) with freshly added EDTA-free protease inhibitor cocktail (Roche). Protein lysate was either directly subject to immunoblot assay or Co-IP. For Co-IP, Lysates were incubated with FLAG magnetic beads (Sigma) overnight at 4° C. The beads were washed with 1×IP lysis buffer 5 times and then eluted with 2×SDS sample buffer.

6. Fluorescence Microscopy

HeLa cell stably expressing GFP-LC3 were washed with PBS two times and fixed with 4% paraformaldehyde (PFA) in PBS on ice for 20 minutes. After washing with PBS three times, cells were mounted with mounting medium (Fluor-Save reagent, Calbiochem). Cells were examined under Leica invert confocal microscope (TCS-SP8-MP system). Images were taken with 63× oil immersion objective lens at room temperature and image acquisition was performed by LAS X software.

7. EGFR Degradation Assay

HEK293T or A549 cells in 6-well plate were washed with PBS two times and serum-starved overnight in DMEM. EGFR endocytosis was induced by incubation with DMEM medium (with 20 mM HEPES and 0.2% BSA) containing 200 ng/mL of EGF (Invitrogen). Cells were collected at each time point after EGF stimulation and lysed in Laemmli sample buffer (62.5 mM Tris-HCl, pH 6.8, 2% SDS, 25% glycerol, 5% β-mercaptoethanol). 20 μg protein lysate was collected for each time point, analyzed by SDS-PAGE and immunoblotted with anti-EGFR antibody (1:2000, Santa Cruz Biotechnology).

8. Computational Design of Stapled Peptides

The 3D structure of the α-helical segment corresponding to residues 191-205 within the Beclin 1 coiled coil domain (PDB ID 3Q8T; SEQ ID NO: 17) was used as the initial model for SP1 (SEQ ID NO: 1). Eleven other SPs (i.e. SP2-SP12; SEQ ID NO: 2-12) were designed by substituting the residues at positions 191, 194, 195, 201 and 205. A hydrocarbon staple of 13-carbon length was added in silico to link residue 197 and 204. The N-terminal of each SP was capped with an acetyl group and the C-terminal was capped with a methylamide group. All of the above molecular modeling tasks were conducted using the Sybyl software (version 8.0).

A molecular dynamics (MD) simulation was conducted to derive the binding mode of each designed SP (SEQ ID NO: 1-12) to the monomer chain of Beclin 1 coiled coil domain. Force field parameters of the stapled region of each SP were prepared using the Antechamber module in the AMBER software (version 14); while the remaining parts of SPs were assigned with FF03SB force field parameters. The complex of Beclin 1 and SP (SEQ ID NO: 1-12) was solvated in a TIP3P water box with a margin of 10 Å at each dimension. The complex structure was first optimized through a stepwise process using the Sander module in AMBER, and then was heated up from 0 K to 300 K in 100 ps. Finally, the complex structure was equilibrated without any restraint for 8 ns under 300 K and 1 atm. Based on the outcomes of MD simulation, the MM-GB/SA method implemented in AMBER was used to compute the binding affinity of each designed SP to Beclin 1. A total of 400 snapshots were sampled from the last 4 ns segment on the entire MD trajectory with an interval of 10 ps. The final binding energy of each SP was computed as the average of the results obtained on these 400 snapshots. Vibrational entropy was not considered here. All parameters used in the MM-GB/SA computation were set to their default values.

9. Synthesis of Stapled Peptide (SP)

The scrambled peptides and SP candidates deemed promising by computational design were acquired commercially from Shanghai ABBiochem Co., Ltd (Shanghai, P.R. China). Chemical structure and purify of the final synthesized products were characterized by HRMS and HPLC.

Results

Structure-Based Rational Design of Beclin 1-Targeting Stapled Peptides

Given the importance of the Beclin 1-UVRAG interaction in facilitating lysosomal degradation of EGFR, small-molecule compounds were designed in the present invention to target the Beclin 1 coiled-coil domain and promote EGFR degradation. Such compounds would have the translational potential to be developed into a novel approach to suppress EGFR-driven proliferation, for example, in cancer cells.

With the target binding site of residues 231-245 (SEQ ID NO: 15) defined, the design of a small library of stapled peptides were proceeded. The model of the first stapled peptide (SP1, SEQ ID NO: 1) was built by simply taking the α-helical segment that interacts with the target region within the Beclin 1 homodimer structure, i.e. the segment covering residues 191-205 (SEQ ID NO: 17), as the prototype. A In one embodiment, examples of peptides include, but not limited to, the peptides described in FIG. 1C. In one embodiment, a stapled peptide (1) with a particular amino acid sequence is designed to target the Beclin 1 coiled coil region spanning residues 231 to 245 (SEQ ID NO: 15). A two-turn hydrocarbon staple is added to stabilize the α-helical structure of the designed peptide. In some embodiments, mutated analogs of peptide (1) are designed.

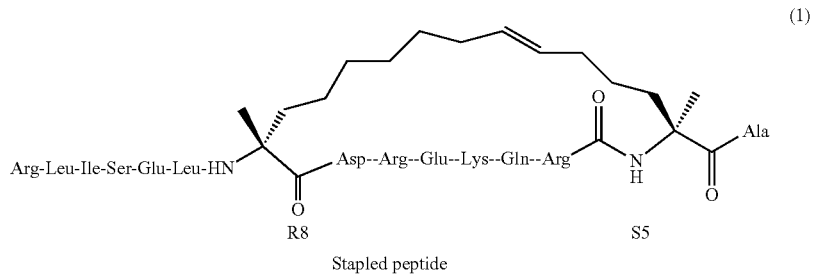

Figure 1B:
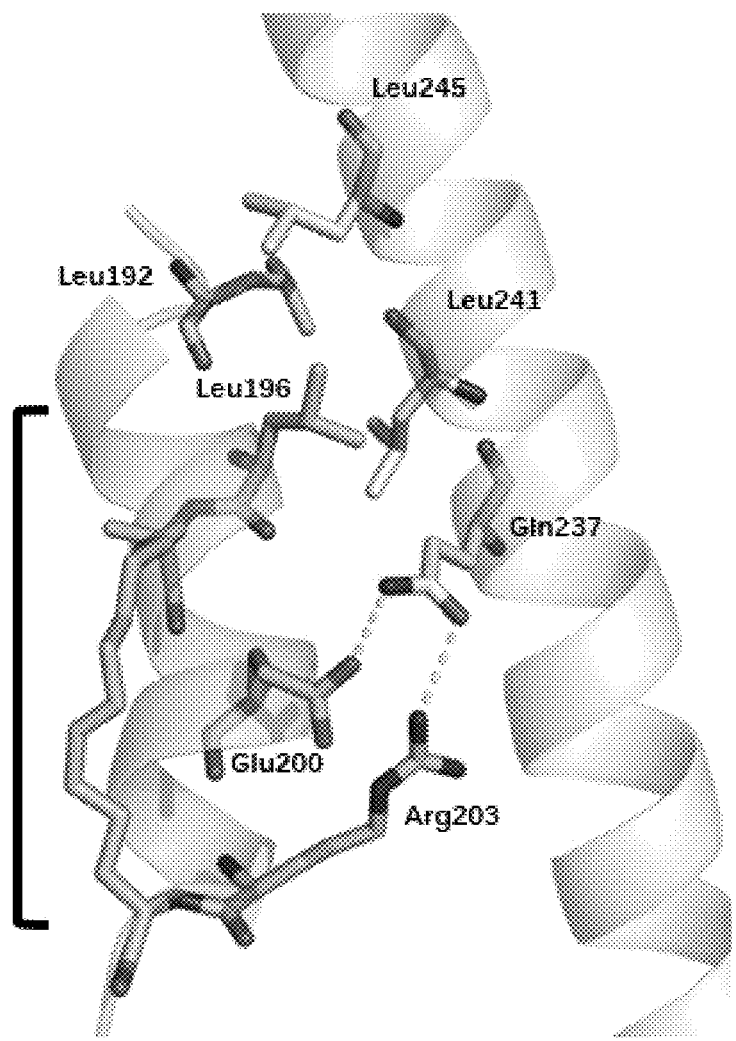
FIG. 1B shows a model of a computationally designed stapled peptide SP1 (SEQ ID NO: 1) binding to the C-terminal region of Beclin 1 coiled coil domain. The bracket highlights the hydrocarbon staple. The residues are numbered according to Beclin 1 sequence.

Stapled peptide hydrocarbon staple was introduced in silico to link residues 197 and 204, both located on the "outer" side of the helix and not involved in coiled coil interface, to help stabilize the α-helical structure but not to interfere with Beclin 1 binding. The structural model of SP1 (SEQ ID NO: 1) binding to Beclin 1 was generated simply by superposing SP1 (SEQ ID NO: 1) onto the Beclin 1 coiled coil homodimer structure (FIG. 1B). Computational optimization to enhance the binding affinity of SP1 (SEQ ID NO: 1) toward the target region was carried out. A library of stapled peptides (SP2-SP12; SEQ ID NO: 2-12) was generated in which residues deemed critical for target site binding were unchanged while other amino acid residues were computationally varied (FIG. 1C). The binding modes of these stapled peptides to the Beclin 1 molecule were characterized by molecular dynamics (MD) simulations and their binding energies were computed using the force field-based MM-GB/SA method. Certain sequence changes, such as replacing Gln194 with Ser and Val205 with Ala in SP4 (SEQ ID NO: 4), led to significantly improved binding energy (FIG. 1C).

Figure 1D:
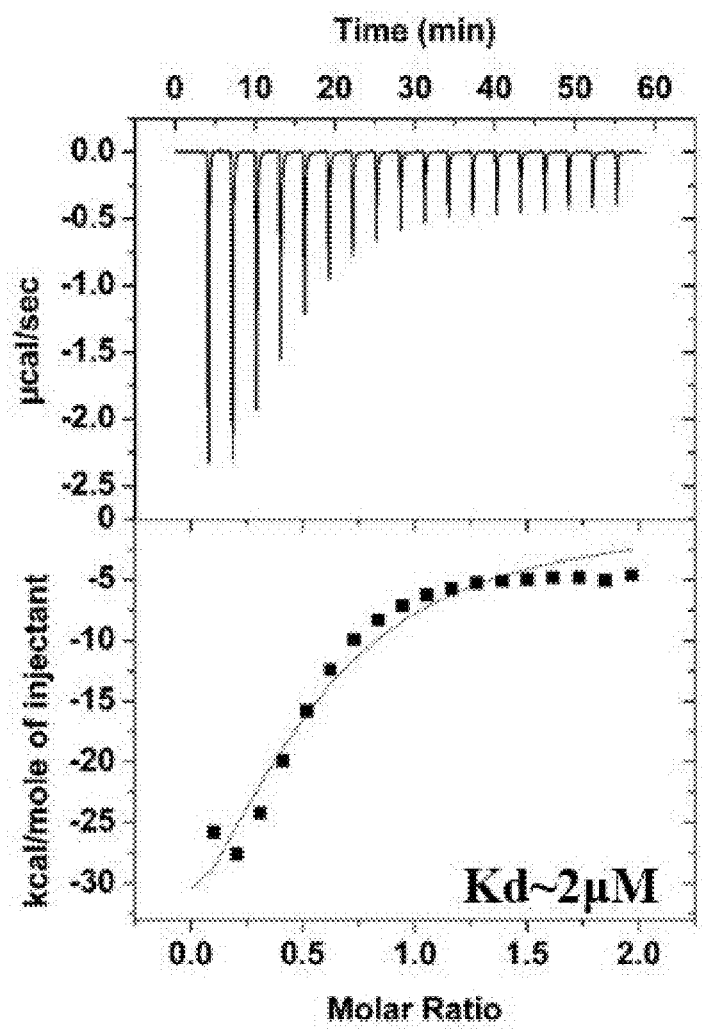
FIG. 1D shows SP4 (SEQ ID NO: 4) binds to Beclin 1 coiled coil domain (Kd=2 μM) as confirmed by ITC measurements.

Tat sequence (SEQ ID NO: 13: YGRKKRRQRRR) was linked in front of all peptides except the rhodamine B labeled one to enhance cell permeability. The computationally optimized stapled peptide SP4 (SEQ ID NO: 4) was chosen and synthesized by a commercial vendor following the synthetic method pioneered by Kim et. al. (Kim, Grossmann et al. 2011) (FIG. 1C). The purified product was confirmed by mass spectroscopy and HPLC. The importance of the hydrocarbon staple in maintaining the α-helical structure of the designed peptide was confirmed by circular dichroism (CD) measurements (FIG. 1D). The CD spectrum of peptide P4, which is the same as SP4 (SEQ ID NO: 4) but without the hydrocarbon staple, showed largely loop-like profile. The CD spectrum of SP4 (SEQ ID NO: 4), however, revealed high α-helical content. ITC profile showed direct interaction between SP4 (SEQ ID NO: 4) and Beclin 1 coiled coil domain with Kd~2 μM, suggesting that this molecule can bind to Beclin 1 coiled coil domain effectively and most likely at the intended target region (FIG. 1D). Furthermore, SP4 (SEQ ID NO: 4) can induce dimer-to-monomer transition in Beclin 1 coiled coil domain. The Light Scattering (LS) profile of Beclin 1 coiled coil domain in absence of SP4 (SEQ ID NO: 4) indicates a homodimer with predicted molecular weight of 24.8 kDa.

In summary, structure-based design of stapled peptides that mimic the Beclin 1 segment of residues 191-205 (SEQ ID NO: 17) can bind to Beclin 1 coiled coil domain with high affinity and render it monomeric to promote Beclin 1-UVRAG interaction. SEQ ID NO: 17 corresponds to amino acids 193-207 of human Beclin 1 (SEQ ID NO: 18).

Figure 2A:
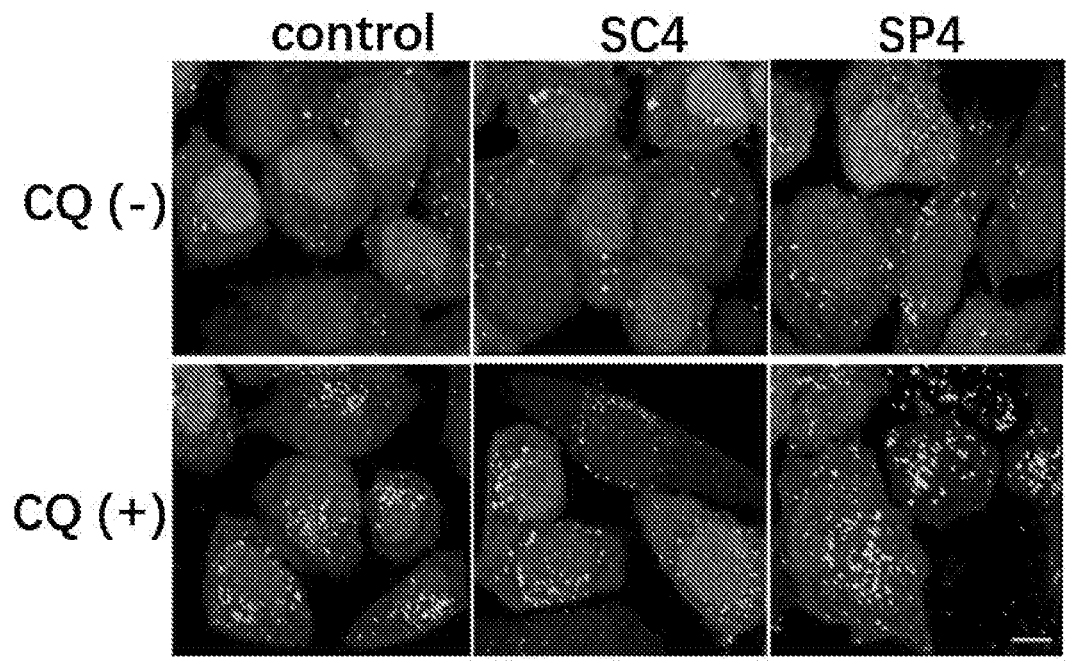
FIG. 2A shows representative confocal fluorescence images of HeLa cells stably expressing GFP-LC3 after treatment with empty vehicle (control), Tat-tagged scrambled peptide (SC4, SEQ ID NO: 14: Ac-RALRIQS-KEELRD-NH2) and Tat-tagged SP4 stapled peptide (SP4, SEQ ID NO: 4). Experiments were done both in the absence (−) or presence (+) of chloroquine.
Figure 2B:
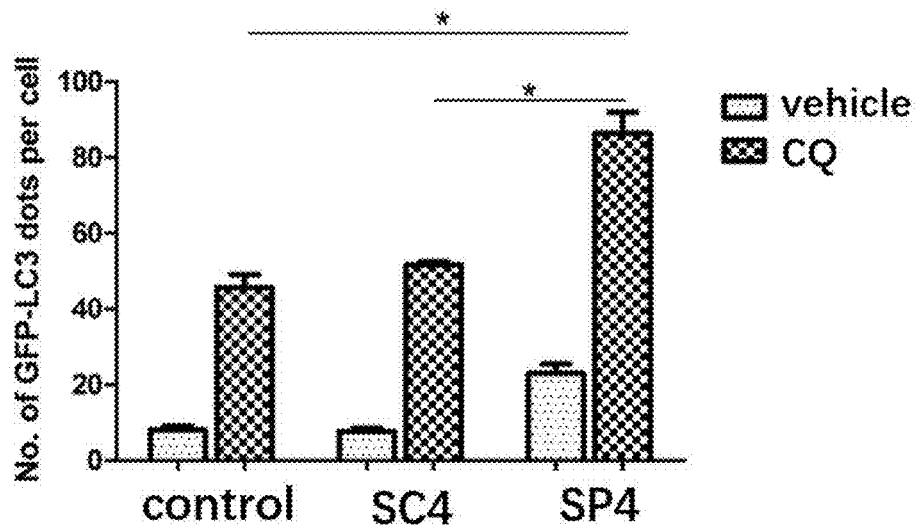
FIG. 2B shows histogram to show quantification of the results from FIG. 2A. Error bars represent ±s.e.m of triplicate samples. Vehicle: empty vector as control. ***P, 0.05. t-test.
Figure 2C:
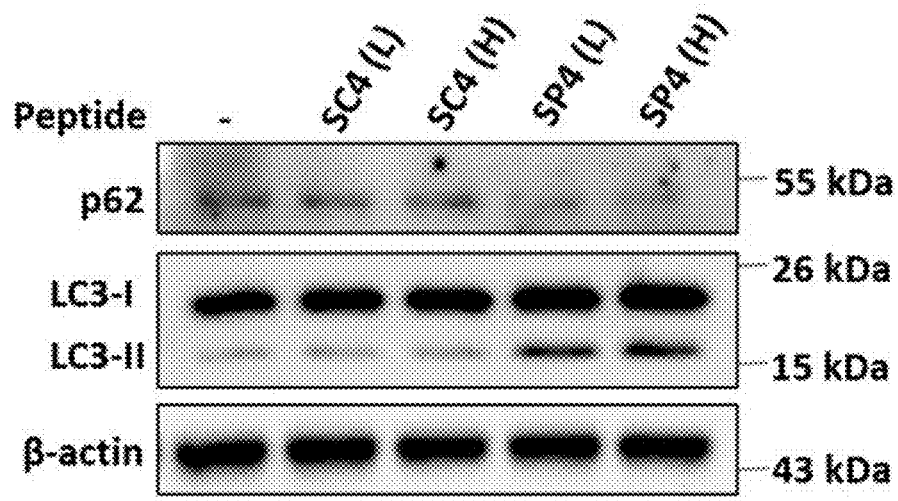
FIG. 2C shows western blots to assess the LC3 lipidation profile in HEK293T cell after treatment with scrambled or stapled peptide at both low dosage (L, 10 μM) and high dosage (H, 20 μM) in the absence of chloroquine (CQ, 50 μM).

Beclin 1-Specific Stapled Peptide Promotes Autophagy and Enhances Lysosomal Degradation of EGFR The biological efficacy of the designed peptide SP4 (SEQ ID NO: 4) in modulating autophagy and lysosomal degradation of EGFR was characterized using cell-based assays. To enhance cell permeability, the HIV Tat sequence (SEQ ID NO: 13) were appended to SP4 (SEQ ID NO: 4) (Tat-stapled) and added it to HeLa cells stably expressing GFP-LC3. A Tat-scrambled peptide was used as control for this experiment in which the sequence of SP4 (SEQ ID NO: 4) was scrambled into random order, without hydrocarbon stable, and appended after the Tat sequence. The results of the present invention showed that Tat380 stapled peptide induced significantly larger number of LC3 puncta as compared to both control and Tat-scrambled, both in the presence and absence of chloroquine (FIGS. 2A and 2B). Similarly, Tat-stapled peptide also led to higher LC3 lipidation rate in these HeLa cells, particularly in the presence of lysosomal inhibitor CQ (FIG. 2C).

Figure 1E:
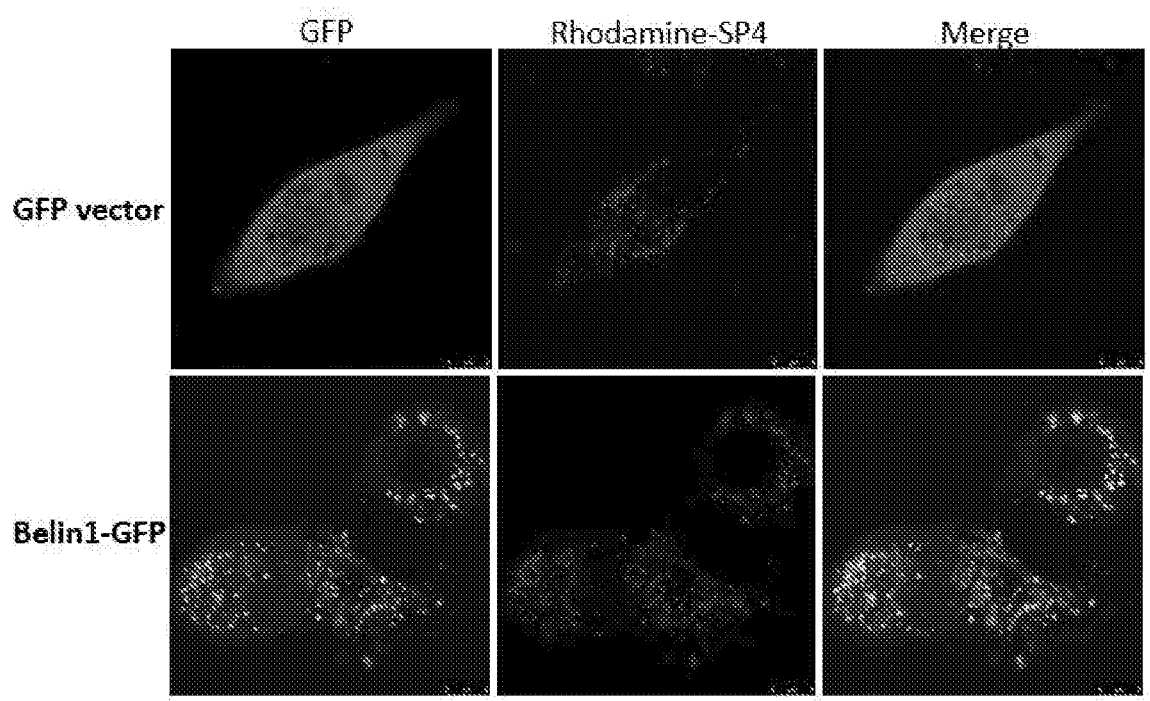
FIG. 1E shows representative confocal fluorescence images of Rhodamine-labeled SP4 (SEQ ID NO: 4) colocalizes with GFP-tagged Beclin 1 in A549 cell. A549 cells transiently expressing GFP-Beclin 1 were treated with 20 μM Rhodamine-SP4 (SEQ ID NO: 4) for 30 minutes and observed under a confocal microscope.
Figure 2D:
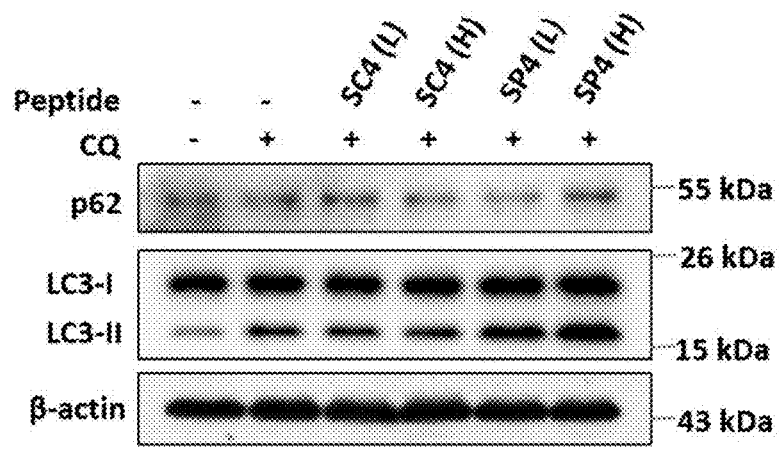
FIG. 2D shows western blots to assess the p62 level and LC3 lipidation profile in HEK293T cell after treatment with scrambled or stapled peptide at both low dosage (L, 10 μM) and high dosage (H, 20 μM) in the presence (+) of chloroquine (CQ, 50 μM).
Figure 2E:
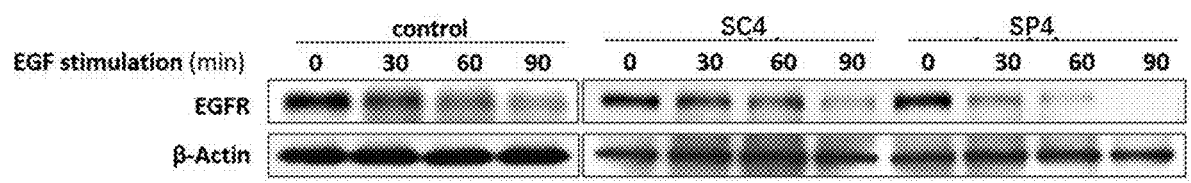
FIG. 2E shows EGFR degradation profile in HEK293T cells after treatment with scrambled or stapled peptides.
Figure 2F:
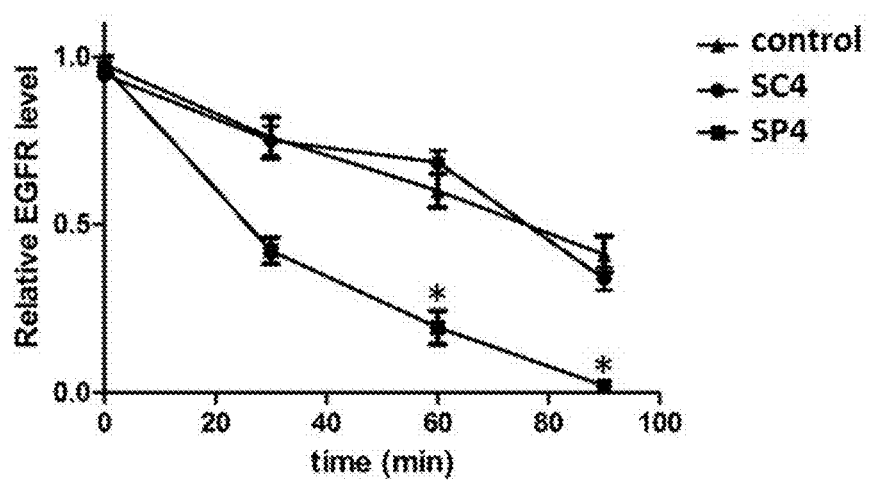
FIG. 2F shows time-dependent plot of FIG. 2E after three independent experiments.
Figure 2G:
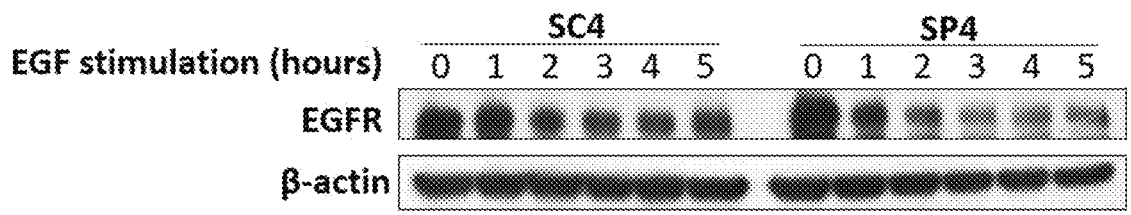
FIG. 2G shows EGFR degradation profile in A549 cells after treatment with scrambled or stapled peptides.
Figure 2H:
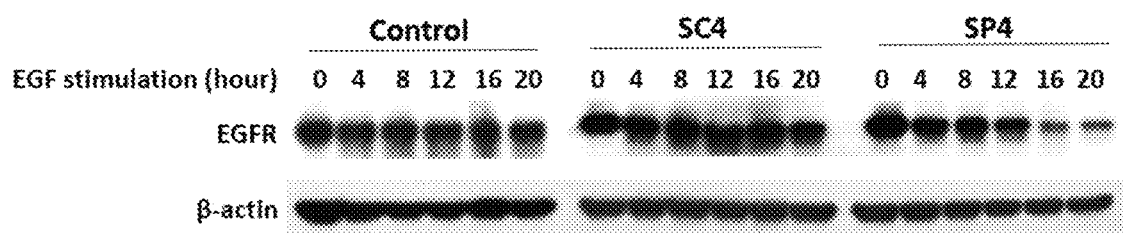
FIG. 2H shows EGFR degradation profile in H1975 cells after treatment with scrambled or stapled peptides.
Figure 2I:
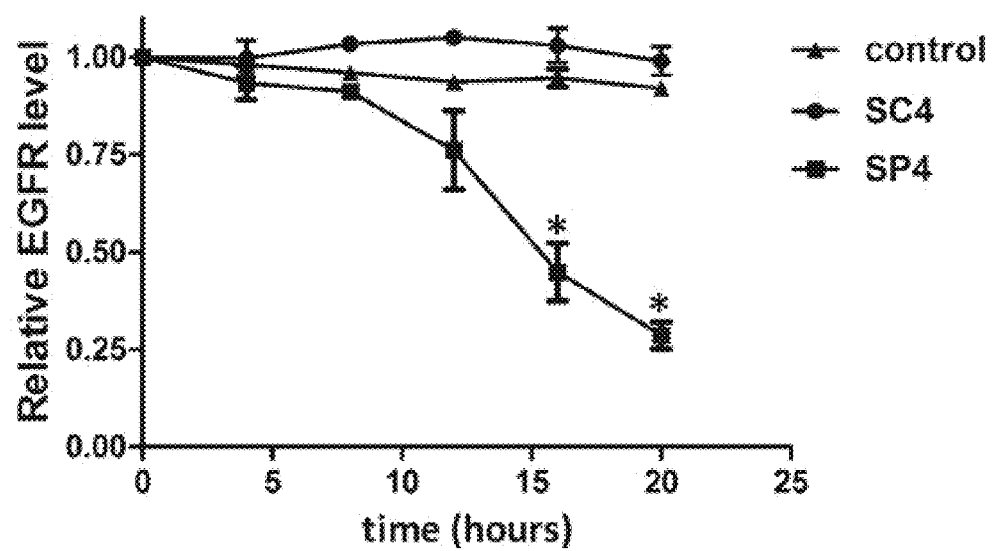
FIG. 2I shows time-dependent plot of FIG. 2H after three independent experiments.

The efficacy of SP4 (SEQ ID NO: 4) was tested in terms of promoting autophagy in NSCLC cells. Rhodamine-labeled SP4 co-localized well with GFP-Beclin 1 in A549 NSCLC cells (FIG. 1E). Treatment of HEK293T cells with SP4 (SEQ ID NO: 4) led to enhanced LC3 lipidation in dosage-dependent manner in the absence or presence of chloroquine (CQ) (FIGS. 2C and 2D). Furthermore, the efficacy of SP4 (SEQ ID NO: 4) was tested in regulating EGFR degradation. Addition of SP4 (SEQ ID NO: 4) to HEK293T cells significantly enhanced EGFR degradation with half-life shortened from more than 90 minutes in the case of control or scrambled peptide to shorter than 30 minutes for SP4 (SEQ ID NO: 4) (FIGS. 2E and 2F). Moreover, SP4 (SEQ ID NO: 4) treatment significantly enhanced EGFR degradation in NSCLCs bearing wild type EGFR (A549 cell line, FIG. 2G) or mutated EGFR (H1975 cell lines, FIGS. 2H and 5I).

In summary, structure-based rational design targeting the Beclin 1 coiled coil domain at region 231-245 (SEQ ID NO: 15) has yielded stapled peptides that specifically bind to Beclin 1 coiled coil domain and render it monomeric to promote Beclin 1-UVRAG interaction. SEQ ID NO: 15 corresponds to amino acids 233-247 of human Beclin 1 (SEQ ID NO: 16).

Collectively, the data of the present invention confirmed that the rationally designed stapled peptide SP4 (SEQ ID NO: 4) can promote autophagy activity and enhance EGFR degradation in a Beclin 1-dependent manner.

Discussion

The direct interaction between Beclin 1 and its two mutually competitive binding partners Atg14L and UVRAG is essential for the formation of functionally distinct Atg14L- or UVRAG-containing Beclin 1-Vps34 subcomplexes. Interestingly, Beclin 1, Atg14L and UVRAG all contain a coiled coil domain that is critical for their respective interactions. It is tempting to propose that these domains can facilitate stable Beclin 1-Atg14L/UVRAG interaction by simply "wrapping" around each other to form coiled coil assemblies. But the molecular mechanism of their specific interactions is not known. In particular, the coiled coil domains of all three proteins contain prominent "imperfect" features, i.e. charged or polar residues are frequently found at a and d positions within the heptad repeat motif where hydrophobic residues are expected. As a result, the coiled coil domains of Atg14L and UVRAG are actually monomeric in vitro while the coiled coil domain of Beclin 1 only forms a metastable homodimer. It is not intuitive how these "imperfect" coils can form stable Beclin 1-Atg14L/UVRAG heterodimeric assemblies.

Lastly, there is intense interest to target the autophagy process for disease modifying therapies. Multiple clinical trials were initiated using autophagy inhibitor CQ in combination with existing cancer drugs to enhance therapeutic efficacy for late-stage refractory cancer types. However, potent and specific modulators of autophagy are lacking because compounds like CQ and mTOR inhibitors are not specific to autophagy and may have off-target effect. A previous study reported a Beclin 1 peptide derived from its membrane-binding region can serve as potent inducer of autophagy and decrease the replication of pathogens in cell- and animal-based models. Here a new strategy is presented for generating Beclin 1 peptides for autophagy modulation. By specifically targeting the Beclin 1 coiled coil domain C-terminal to the UVRAG binding site, rationally designed Beclin 1 peptides with hydrocarbon staples to stabilize their α-helical structure can bind to functionally inactive Beclin 1 homodimer in the reserve pool, assist its dimer-to-monomer transition and promote the formation of Atg14L/UVRAG containing Beclin 1-Vps34 complexes. As a result, both Vps34-dependent autophagy and endocytic trafficking can be enhanced, resulting in enhanced lysosomal degradation of EGFR and possibly inhibition of EGFR-driven cancer cell proliferation.

The approach of the present invention provides a novel Beclin 1-specific strategy to target the Beclin 1-Vps34 complex for EGFR-based anti-cancer treatment. Furthermore, as recent studies have implicated the UVRAG-containing Beclin 1-Vps34 complex in endocytic degradation of multiple membrane receptors such as insulin receptor (IR) and TGF-β receptor ALK5, the design strategy presented herein can be applied to these processes as well.

REFERENCES

1. High-throughput structure determination. Proceedings of the 2002 CCP4 (Collaborative Computational Project in Macromolecular Crystallography) study weekend. January, 2002. York, United Kingdom. Acta Crystallogr D Biol Crystallogr 58, 1897-1970.
2. High-throughput structure determination. Proceedings of the 2002 CCP4 (Collaborative Computational Project in Macromolecular Crystallography) study weekend. January, 2002. York, United Kingdom. Acta Crystallogr D Biol Crystallogr 58, 1897-1970.
3. Adi-Harel, S., Erlich, S., Schmukler, E., Cohen-Kedar, S., Segev, O., Mizrachy, L., Hirsch, J. A., and Pinkas-Kramarski, R. (2010). Beclin 1 self-association is independent of autophagy induction by amino acid deprivation and rapamycin treatment. J Cell Biochem 110, 1262-1271.
4. Emsley, P., and Cowtan, K. (2004). Coot: model-building tools for molecular graphics. Acta Crystallogr D Biol Crystallogr 60, 2126-2132.
5. He, C., and Levine, B. (2010). The Beclin 1 interactome. Curr Opin Cell Biol 22, 140-149.
6. Li, X., He, L., Che, K. H., Funderburk, S. F., Pan, L., Pan, N., Zhang, M., Yue, Z., and Zhao, Y. (2012a). Imperfect interface of Beclin 1 coiled-coil domain regulates homodimer and heterodimer formation with Atg14L and UVRAG. Nat Commun 3, 662.
7. Li, X., He, L., Zhang, M., Yue, Z., and Zhao, Y. (2012b). The BECN1 coiled coil domain: an "imperfect" homodimer interface that facilitates ATG14 and UVRAG binding. Autophagy 8, 1258-1260.
8. Liang, C., Feng, P., Ku, B., Dotan, I., Canaani, D., Oh, B. H., and Jung, J. U. (2006). Autophagic and tumour suppressor activity of a novel Beclin 1-binding protein UVRAG. Nat Cell Biol 8, 688-699.
9. Liang, C., Feng, P., Ku, B., Oh, B. H., and Jung, J. U. (2007). UVRAG: a new player in autophagy and tumor cell growth. Autophagy 3, 69-71.
10. Liang, C., Lee, J. S., Inn, K. S., Gack, M. U., Li, Q., Roberts, E. A., Vergne, I., Deretic, V., Feng, P., Akazawa, C., et al. (2008a). Beclin 1-binding UVRAG targets the class C Vps complex to coordinate autophagosome maturation and endocytic trafficking. Nat Cell Biol 10, 776-787.
11. Liang, C., Sir, D., Lee, S., Ou, J. H., and Jung, J. U. (2008b). Beyond autophagy: the role of UVRAG in membrane trafficking. Autophagy 4, 817-820.
12. Matsunaga, K., Saitoh, T., Tabata, K., Omori, H., Satoh, T., Kurotori, N., Maejima, I., Shirahama-Noda, K., Ichimura, T., Isobe, T., et al. (2009). Two Beclin 1-binding proteins, Atg14L and Rubicon, reciprocally regulate autophagy at different stages. Nat Cell Biol 11, 385-396.
13. Murshudov, G. N., Vagin, A. A., and Dodson, E. J. (1997). Refinement of macromolecular structures by the maximum-likelihood method. Acta Crystallogr D Biol Crystallogr 53, 240-255.
14. Noble, C. G., Dong, J. M., Manser, E., and Song, H. (2008). Bcl-xL and UVRAG cause a monomer-dimer switch in Beclin 1. J Biol Chem 283, 26274-26282.
15. Perelman, B., Dafni, N., Naiman, T., Eli, D., Yaakov, M., Feng, T. L., Sinha, S., Weber, G., Khodaei, S., Sancar, A., et al. (1997). Molecular cloning of a novel human gene encoding a 63-kDa protein and its sublocalization within the 11q13 locus. Genomics 41, 397-405.
16. Potterton, L., McNicholas, S., Krissinel, E., Gruber, J., Cowtan, K., Emsley, P., Murshudov, G. N., Cohen, S., Perrakis, A., and Noble, M. (2004). Developments in the CCP4 molecular-graphics project. Acta Crystallogr D Biol Crystallogr 60, 2288-2294.

17. Takahashi, Y., Coppola, D., Matsushita, N., Cualing, H. D., Sun, M., Sato, Y., Liang, C., Jung, J. U., Cheng, J. Q., Mule, J. J., et al. (2007). Bif-1 interacts with Beclin 1 through UVRAG and regulates autophagy and tumorigenesis. Nat Cell Biol 9, 1142-1151.
18. Takahashi, Y., Meyerkord, C. L., and Wang, H. G. (2009). Bif-1/endophilin B1: a candidate for crescent driving force in autophagy. Cell Death Differ 16, 947-955.
19. Terwilliger, T. C., and Berendzen, J. (1999). Automated MAD and MIR structure solution. Acta Crystallogr D Biol Crystallogr 55, 849-861.
20. Zhao, Z., Oh, S., Li, D., Ni, D., Pirooz, S. D., Lee, J. H., Yang, S., Lee, J. Y., Ghozalli, I., Costanzo, V., et al. (2012). A dual role for UVRAG in maintaining chromosomal stability independent of autophagy. Dev Cell 22, 1001-1016.
21. Zhong, Y., Wang, Q. J., Li, X., Yan, Y., Backer, J. M., Chait, B. T., Heintz, N., and Yue, Z. (2009). Distinct regulation of autophagic activity by Atg14L and Rubicon associated with Beclin 1-phosphatidylinositol-3-kinase complex. Nat Cell Biol 11, 468-476.
22. U.S. Pat. No. 8,802,633, Autophagy-inducing peptide analogs, Published on Aug. 12, 2014.
23. (2002). "High-throughput structure determination. Proceedings of the 2002 CCP4 (Collaborative Computational Project in Macromolecular Crystallography) study weekend. January, 2002. York, United Kingdom." Acta Crystallogr D Biol Crystallogr 58(Pt 11): 1897-1970.
24. Bricogne, G., et al. (2003). "Generation, representation and flow of phase information in structure determination: recent developments in and around SHARP 2.0." Acta Crystallogr D Biol Crystallogr 59(Pt 11): 2023-2030.
25. Emsley, P. and K. Cowtan (2004). "Coot: model-building tools for molecular graphics." Acta Crystallogr D Biol Crystallogr 60(Pt 12 Pt 1): 2126-2132.
26. Kim, Y. W., et al. (2011). "Synthesis of all-hydrocarbon stapled alpha-helical peptides by ring-closing olefin metathesis." Nat Protoc 6(6): 761-771.
27. Li, X., et al. (2012). "Imperfect interface of Beclin 1 coiled-coil domain regulates homodimer and heterodimer formation with Atg14L and UVRAG." Nat Commun 3: 662.
28. Li, X., et al. (2012). "Imperfect interface of Beclin 1 coiled-coil domain regulates homodimer and heterodimer formation with Atg14L and UVRAG." NATURE COMMUNICATIONS 3: 662.
29. Li, X., et al. (2012). "The BECN1 coiled coil domain: an "imperfect" homodimer interface that facilitates ATG14 and UVRAG binding." Autophagy 8(8): 1258-1260.
30. Liang, C., et al. (2006). "Autophagic and tumour suppressor activity of a novel Beclin 1-binding protein UVRAG." Nat Cell Biol 8(7): 688-699.
31. Liang, C., et al. (2007). "UVRAG: a new player in autophagy and tumor cell growth." Autophagy 3(1): 69-71.
32. Liang, C., et al. (2008). "Beclin 1-binding UVRAG targets the class C Vps complex to coordinate autophagosome maturation and endocytic trafficking." Nat Cell Biol 10(7): 776-787.
33. Liang, C., et al. (2008). "Beyond autophagy: the role of UVRAG in membrane trafficking." Autophagy 4(6): 817-820.
34. Matsunaga, K., et al. (2009). "Two Beclin 1-binding proteins, Atg14L and Rubicon, reciprocally regulate autophagy at different stages." Nat Cell Biol 11(4): 385-396.
35. McKnight, N. C., et al. (2014). "Beclin 1 is required for neuron viability and regulates endosome pathways via the UVRAG-VPS34 complex." PLoS Genet 10(10): e1004626.
36. Murshudov, G. N., et al. (1997). "Refinement of macromolecular structures by the maximum-likelihood method." Acta Crystallogr D Biol Crystallogr 53(Pt 3): 240-255.
37. Otwinowski, Z. and W. Minor (1997). "Processing of X-ray diffraction data collected in oscillation mode." Methods Enzymol 276: 307-326.
38. Perelman, B., et al. (1997). "Molecular cloning of a novel human gene encoding a 63-kDa protein and its sublocalization within the 11q13 locus." Genomics 41(3): 397-405.
39. Potterton, L., et al. (2004). "Developments in the CCP4 molecular-graphics project." Acta Crystallogr D Biol Crystallogr 60(Pt 12 Pt 1): 2288-2294.
40. Rostislavleva, K., et al. (2015). "Structure and flexibility of the endosomal Vps34 complex reveals the basis of its function on membranes." Science 350(6257): aac7365.
41. Takahashi, Y., et al. (2007). "Bif-1 interacts with Beclin 1 through UVRAG and regulates autophagy and tumorigenesis." Nat Cell Biol 9(10): 1142-1151.
42. Takahashi, Y., et al. (2009). "Bif-1/endophilin B1: a candidate for crescent driving force in autophagy." Cell Death Differ 16(7): 947-955.
43. Terwilliger, T. C. and J. Berendzen (1999). "Automated MAD and MIR structure solution." Acta Crystallogr D Biol Crystallogr 55(Pt 4): 849-861.
44. Zhao, Z., et al. (2012). "A dual role for UVRAG in maintaining chromosomal stability independent of autophagy." Dev Cell 22(5): 1001-1016.
45. Zhong, Y., et al. (2009). "Distinct regulation of autophagic activity by Atg14L and Rubicon associated with Beclin 1-phosphatidylinositol-3-kinase complex." Nat Cell Biol 11(4): 468-476.

What is claimed is:

1. A hydrocarbon-stapled polypeptide designed to target Beclin 1, selected from the group consisting of SEQ ID NOs: 1-12.

2. A pharmaceutical composition comprising the hydrocarbon-stapled polypeptide of claim 1.

3. The pharmaceutical composition of claim 2, further comprising one or more pharmaceutically acceptable excipients, vehicles or carriers.

4. The pharmaceutical composition of claim 2, wherein said pharmaceutical composition is formulated in the form of a cream, gel, ointment, suppository, tablet, granule, injection, powder, solution, suspension, spray, patch or capsule.

5. A method of enhancing autophagy or endocytic trafficking, comprising the step of contacting a population of cells with the pharmaceutical composition of claim 2, thereby enhancing lysosomal degradation of one or more target proteins.

6. The method of claim 5, wherein the target protein is EGFR.

7. A method of anti-cancer therapy for enhancing EGFR degradation in cancers exhibiting EGFR-driven cell proliferation, the method comprising administering a therapeutically effective amount of the pharmaceutical composition of claim 2 to a subject in need thereof.

8. The method of claim 7, wherein the subject is a vertebrate, a mammal or human.

9. The method of claim 7, wherein the subject has a cancer selected from the group consisting of non-small cell lung cancer (NSCLC), colorectal cancer, ovarian cancer, glioblastoma, and breast cancer.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
```

```
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 1

Arg Leu Ile Gln Glu Leu Xaa Asp Arg Glu Ala Gln Arg Xaa Val
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 2

Arg Leu Ile Gln Glu Leu Xaa Asp Arg Glu Ala Gln Arg Xaa Ser
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 3

Arg Leu Ile Ser Glu Leu Xaa Asp Arg Glu Lys Gln Arg Xaa Val
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 4

Arg Leu Ile Ser Glu Leu Xaa Asp Arg Glu Lys Gln Arg Xaa Ala
1               5                   10                  15
```

<210> SEQ ID NO 5
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 5

Arg Leu Ile Gln Glu Leu Xaa Asp Arg Glu Lys Gln Arg Xaa Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 6

Arg Leu Ile Ser Glu Leu Xaa Asp Arg Glu Lys Gln Arg Xaa Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 7

Arg Leu Ile Gln Glu Leu Xaa Asp Arg Glu Lys Gln Arg Xaa Arg
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE

```
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 8

Arg Leu Ile Gln Glu Leu Xaa Asp Arg Glu Lys Glu Arg Xaa Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 9

Leu Leu Ile Ser Glu Leu Xaa Asp Arg Glu Lys Gln Arg Xaa Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 10

Arg Leu Leu Ser Glu Leu Xaa Asp Arg Glu Lys Gln Arg Xaa Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 11
```

Leu Leu Leu Ser Arg Leu Xaa Asp Arg Glu Lys Gln Arg Xaa Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: Xaa = (R)-2-amino-2-methyldec-9-enoic acid
      residue
<220> FEATURE:
<221> NAME/KEY: MISC_FEATURE
<222> LOCATION: (14)..(14)
<223> OTHER INFORMATION: Xaa = (S)-2-amino-2-methylhept-6-enoic acid
      residue

<400> SEQUENCE: 12

Leu Leu Ile Ser Gln Leu Xaa Asp Arg Glu Lys Gln Arg Xaa Ala
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 13

Tyr Gly Arg Lys Lys Arg Arg Gln Arg Arg Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 14

Arg Ala Leu Arg Ile Gln Ser Lys Glu Glu Leu Arg Asp
1               5                   10

<210> SEQ ID NO 15
<211> LENGTH: 15
<212> TYPE: PRT
<213> ORGANISM: Unknown
<220> FEATURE:
<223> OTHER INFORMATION: Beclin 1

<400> SEQUENCE: 15

Tyr Ser Glu Phe Lys Arg Gln Gln Leu Glu Leu Asp Asp Glu Leu
1               5                   10                  15

<210> SEQ ID NO 16
<211> LENGTH: 15
<212> TYPE: PRT
<213> ORGANISM: Unknown
<220> FEATURE:
<223> OTHER INFORMATION: Human Beclin 1

<400> SEQUENCE: 16

Tyr Ser Glu Phe Lys Arg Gln Gln Leu Glu Leu Asp Asp Glu Leu
1               5                   10                  15

```
<210> SEQ ID NO 17
<211> LENGTH: 15
<212> TYPE: PRT
<213> ORGANISM: Unknown
<220> FEATURE:
<223> OTHER INFORMATION: Rat Beclin 1

<400> SEQUENCE: 17

Arg Leu Ile Gln Glu Leu Glu Asp Val Glu Lys Asn Arg Lys Val
1               5                  10                  15

<210> SEQ ID NO 18
<211> LENGTH: 15
<212> TYPE: PRT
<213> ORGANISM: Unknown
<220> FEATURE:
<223> OTHER INFORMATION: Human Beclin 1

<400> SEQUENCE: 18

Arg Leu Ile Gln Glu Leu Glu Asp Val Glu Lys Asn Arg Lys Ile
1               5                  10                  15

<210> SEQ ID NO 19
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 19

Asp Ser Glu Gln Ala Gln Arg Glu Leu Lys Glu Leu Ala Leu Glu Glu
1               5                   10                  15

Glu Arg Leu Ile Gln Glu Leu Glu Asp Val Glu Lys Asn Arg Lys Val
                20                  25                  30

Val Ala Glu Asn Leu Glu Lys Val Gln Ala Glu Ala Glu Arg Leu Asp
            35                  40                  45

Gln Glu Gly Ser Gly Ser Gly Ser Gly Ser Thr Ser Asn Glu
        50                  55                  60

Leu Lys Lys Glu Ser Glu Ser Leu Arg Leu Lys Ile Leu Val Leu Arg
65                  70                  75                  80

Asn Glu Leu Glu Arg Gln Lys Lys Ala Leu Gly Arg Glu Val Ala Phe
                85                  90                  95

Leu His Lys Gln Gln Met Ala Leu Gln Asp Lys Gly
            100                 105

<210> SEQ ID NO 20
<211> LENGTH: 698
<212> TYPE: PRT
<213> ORGANISM: Unknown
<220> FEATURE:
<223> OTHER INFORMATION: UVRAG

<400> SEQUENCE: 20

Met Ser Ser Cys Ala Ser Leu Gly Gly Pro Val Pro Leu Pro Pro Pro
1               5                   10                  15

Gly Pro Ser Ala Ala Leu Thr Ser Gly Ala Pro Ala Arg Ala Leu His
                20                  25                  30

Val Glu Leu Pro Ser Gln Gln Arg Arg Leu Arg His Leu Arg Asn Ile
            35                  40                  45

Ala Ala Arg Asn Ile Val Asn Arg Asn Gly His Gln Leu Leu Asp Thr
        50                  55                  60
```

```
Tyr Phe Thr Leu His Leu Cys Asp Asn Glu Lys Ile Phe Lys Glu Phe
 65                  70                  75                  80
Tyr Arg Ser Glu Val Ile Lys Asn Ser Leu Asn Pro Thr Trp Arg Ser
                 85                  90                  95
Leu Asp Phe Gly Ile Met Pro Asp Arg Leu Asp Thr Ser Val Ser Cys
            100                 105                 110
Phe Val Val Lys Ile Trp Gly Gly Lys Glu Ala Phe Gln Leu Leu
        115                 120                 125
Ile Glu Trp Lys Val Tyr Leu Asp Gly Leu Lys Tyr Leu Gly Gln Gln
    130                 135                 140
Ile His Ala Arg Asn Gln Asn Glu Ile Ile Phe Gly Leu Asn Asp Gly
145                 150                 155                 160
Tyr Tyr Gly Ala Pro Cys Glu His Lys Gly His Pro Asn Ala Gln Lys
                165                 170                 175
Asn Leu Leu Gln Val Asp Gln Asn Cys Val Arg Asn Ser Tyr Asp Val
            180                 185                 190
Phe Ser Leu Leu Arg Leu His Arg Ala Gln Cys Ala Ile Lys Gln Thr
        195                 200                 205
Gln Val Thr Val Gln Arg Leu Gly Lys Glu Ile Glu Glu Lys Leu Arg
    210                 215                 220
Leu Thr Ser Thr Ser Asn Glu Leu Lys Lys Glu Ser Glu Cys Leu Arg
225                 230                 235                 240
Leu Lys Ile Leu Val Leu Arg Asn Glu Leu Glu Arg Gln Lys Lys Ala
                245                 250                 255
Leu Gly Arg Glu Val Ala Phe Leu His Lys Gln Gln Met Ala Leu Gln
            260                 265                 270
Asp Lys Gly Ser Ala Phe Ser Thr Glu His Gly Lys Leu Gln Leu Gln
        275                 280                 285
Lys Asp Ser Leu Ser Glu Leu Arg Lys Glu Cys Thr Ala Lys Arg Glu
    290                 295                 300
Leu Phe Leu Lys Thr Asn Ala Gln Leu Thr Ile Arg Cys Arg Gln Leu
305                 310                 315                 320
Leu Ser Glu Leu Ser Tyr Ile Tyr Pro Ile Asp Leu Asn Glu His Lys
                325                 330                 335
Asp Tyr Phe Val Cys Gly Val Lys Leu Pro Asn Ser Glu Asp Phe Gln
            340                 345                 350
Ala Lys Glu Asp Gly Ser Ile Ala Val Ala Leu Gly Tyr Thr Ala His
        355                 360                 365
Leu Val Ser Met Ile Ser Phe Phe Leu Gln Val Pro Leu Arg Tyr Pro
    370                 375                 380
Ile Ile His Lys Gly Ser Arg Ser Thr Ile Lys Asp Asn Ile Asn Asp
385                 390                 395                 400
Lys Leu Thr Glu Lys Glu Arg Glu Phe Pro Leu Tyr Pro Lys Gly Gly
                405                 410                 415
Glu Lys Leu Gln Phe Asp Tyr Gly Val Tyr Leu Leu Asn Lys Asn Ile
            420                 425                 430
Ala Gln Leu Arg Tyr Gln His Gly Leu Gly Thr Pro Asp Leu Arg Gln
        435                 440                 445
Thr Leu Pro Asn Leu Lys Asn Phe Met Glu His Gly Leu Met Val Arg
    450                 455                 460
Cys Asp Arg His His Ile Ser Asn Ala Ile Pro Val Pro Lys Arg Gln
465                 470                 475                 480
Ser Ser Thr Phe Gly Gly Ala Asp Gly Gly Phe Ser Ala Gly Ile Pro
```

-continued

```
                        485                 490                 495
Ser Pro Asp Lys Val His Arg Lys Arg Ala Ser Ser Glu Asn Glu Arg
            500                 505                 510

Leu Gln Tyr Lys Thr Pro Pro Pro Ser Tyr Asn Ser Ala Leu Thr Gln
            515                 520                 525

Pro Gly Val Ala Met Pro Thr Ser Gly Asp Ser Glu Arg Lys Val Ala
            530                 535                 540

Pro Leu Ser Ser Ser Leu Asp Thr Ser Leu Asp Phe Ser Lys Glu Asn
545                 550                 555                 560

Lys Lys Ala Gly Val Asp Leu Gly Ser Ser Val Ser Gly Asp His Gly
            565                 570                 575

Asn Ser Asp Ser Gly Gln Glu Gln Gly Glu Ala Leu Pro Gly His Leu
            580                 585                 590

Ala Ala Val Asn Gly Thr Ala Leu Pro Ser Glu Gln Ala Gly Pro Ala
            595                 600                 605

Gly Thr Leu Leu Pro Gly Ser Cys His Pro Ala Pro Ser Ala Glu Leu
            610                 615                 620

Cys Cys Ala Val Glu Gln Ala Glu Glu Ile Ile Gly Leu Glu Ala Thr
625                 630                 635                 640

Gly Phe Thr Ser Gly Asp Gln Leu Glu Ala Leu Ser Cys Ile Pro Val
            645                 650                 655

Asp Ser Ala Val Ala Val Glu Cys Asp Glu Gln Val Leu Gly Glu Phe
            660                 665                 670

Glu Glu Phe Ser Arg Arg Ile Tyr Ala Leu Ser Glu Asn Val Ser Ser
            675                 680                 685

Phe Arg Arg Pro Arg Arg Ser Ser Asp Lys
690                 695
```